(12) United States Patent  (10) Patent No.: US 7,901,373 B2
Tavger  (45) Date of Patent: Mar. 8, 2011

(54) HIGH VELOCITY LIQUID-GAS MIST TISSUE ABRASION DEVICE

(75) Inventor: Michael Tavger, Katzrin (IL)

(73) Assignee: TavTech Ltd., Yehud (IL)

( * ) Notice: Subject to any disclaimer, the term of this patent is extended or adjusted under 35 U.S.C. 154(b) by 652 days.

(21) Appl. No.: 10/584,760

(22) PCT Filed: Jan. 5, 2005

(86) PCT No.: PCT/IL2005/000017
§ 371 (c)(1),
(2), (4) Date: Oct. 25, 2007

(87) PCT Pub. No.: WO2005/065032
PCT Pub. Date: Jul. 21, 2005

(65) Prior Publication Data
US 2008/0319453 A1  Dec. 25, 2008

(30) Foreign Application Priority Data
Jan. 8, 2004 (IL) .......................... 159783

(51) Int. Cl.
*A61M 37/00* (2006.01)
(52) U.S. Cl. ....................................................... 604/24
(58) Field of Classification Search ................... 433/88, 433/215; 604/23–27, 30, 39
See application file for complete search history.

(56) References Cited

U.S. PATENT DOCUMENTS

| | | |
|---|---|---|
| 3,982,965 A | 9/1976 | Spotz |
| 4,350,158 A | 9/1982 | Hudson |
| 4,681,264 A | 7/1987 | Johnson, Jr. |
| 4,982,730 A | 1/1991 | Lewis, Jr. |
| 5,012,797 A * | 5/1991 | Liang et al. ................ 601/2 |
| 5,013,241 A | 5/1991 | von Gutfeld et al. |
| 5,022,414 A * | 6/1991 | Muller ..................... 128/898 |
| 5,046,486 A | 9/1991 | Grulke et al. |
| 5,090,904 A * | 2/1992 | Bailey ..................... 433/88 |
| 5,094,615 A | 3/1992 | Bailey |
| 5,100,412 A | 3/1992 | Rosso |
| 5,203,698 A | 4/1993 | Blake et al. |
| 5,207,234 A | 5/1993 | Rosso |
| 5,273,428 A | 12/1993 | Fischer |
| 5,387,182 A | 2/1995 | Otani |
| 5,551,909 A | 9/1996 | Bailey |
| 5,667,483 A | 9/1997 | Santos |
| 5,730,806 A | 3/1998 | Caimi et al. |

(Continued)

FOREIGN PATENT DOCUMENTS

DE  3726349  12/1989

(Continued)

*Primary Examiner* — Manuel A Mendez
(74) *Attorney, Agent, or Firm* — Fay Sharpe LLP (57) ABSTRACT

The present invention relates to a device for abrading or cleansing tissue. The device includes a gas inlet port connected to a pressurized gas source, and a liquid inlet port connected to a pressurized liquid source. There is, additionally, a mist jet delivery nozzle arrangement, which includes one or more gas discharge nozzles arranged to receive a flow of pressurized gas from the gas inlet port and configured to accelerate the flow of gas so as to discharge it at an elevated velocity. Further, there are one or more liquid discharge nozzles arranged to receive a flow of liquid from the liquid inlet port and operative to discharge the flow of liquid into the elevated velocity flow of gas, thereby to similarly accelerate the velocity of the discharged liquid as a mist of accelerated droplets.

31 Claims, 10 Drawing Sheets

U.S. PATENT DOCUMENTS

| | | | |
|---|---|---|---|
| 5,810,842 | A | 9/1998 | Di Fiore et al. |
| 6,120,755 | A | 9/2000 | Jacobs |
| 6,168,577 | B1 | 1/2001 | Niederjohn et al. |
| 6,199,773 | B1 | 3/2001 | Holt et al. |
| 6,203,406 | B1 | 3/2001 | Rose et al. |
| 6,224,378 | B1 | 5/2001 | Valdes et al. |
| 6,293,498 | B1 | 9/2001 | Stanko et al. |
| 6,360,992 | B1 | 3/2002 | Stanko et al. |
| 6,432,113 | B1 | 8/2002 | Parkin et al. |
| 6,454,871 | B1 | 9/2002 | Labib et al. |
| 6,497,572 | B2 | 12/2002 | Hood et al. |

FOREIGN PATENT DOCUMENTS

| | | |
|---|---|---|
| DE | 19654098 | 6/1998 |
| FR | 2599244 | 12/1987 |
| FR | 2654331 | 5/1991 |
| GB | 1008503 | 10/1965 |
| IL | 118801 | 12/2001 |
| IL | 122016 | 12/2001 |
| JP | 2002000620 | 1/2002 |
| KR | 10-2001-0065418 | 7/2001 |
| KR | 10-2005-0093276 | 9/2005 |
| WO | WO 99/23951 | 5/1999 |

* cited by examiner

HIGH VELOCITY LIQUID-GAS MIST TISSUE ABRASION DEVICE

FIELD OF THE INVENTION

The present invention relates, generally to a device for tissue abrasion, and, more specifically, to a device for applying a high velocity liquid-gas mist for dermal abrasion and skin peeling.

BACKGROUND OF THE INVENTION

It is known in the art to provide apparatus for dermal abrasion and the cleansing of exposed in vivo tissue. There are a multiplicity of applications to both humans and animals during surgical procedures where the removal from the tissue surface of solid contaminants, such as fibers, dust, sand particles, and the like, as well as organic matter, such as puss, fats, and others, is necessary.

In addition, such cleansing is necessary in preparation prior to and/or subsequent to treatment for dental conditions such as gingivitis, caused by the long-term effects of plaque deposits. Unremoved plaque mineralizes into a hard deposit called calculus (tartar) that becomes trapped at the base of the tooth. It is also necessary to remove the toxins produced by the bacteria.

Organic matter including the outer dermal layer tends to bond to tissue much more strongly than non-organic matter, and is generally more difficult to remove. Accordingly, while non-organic matter is removable from the tissue by means of a liquid stream, it is often not possible to remove some organic matter in this way. More specifically, and most problematic, are those particles which are smaller than the thickness of the boundary layer of the fluid stream which is formed on the tissue surface during irrigation with a liquid such as water. The boundary layer is characterized by having a fluid velocity which reduces sharply adjacent to the flow surface, and which is virtually zero at the surface.

The smallest particles located in the boundary layer exhibit a drag resistance of a magnitude sufficient for these particles to remain attached to the surface and to resist being swept away by the fluid stream, even if this has an overall very high velocity.

A number of cleansing devices and systems have been developed to improve the cleansing of a variety of surfaces. To attempt solve this problem, there have been developed a number of prior art devices such as disclosed in U.S. Pat. Nos. 3,982,965, 4,350,158, 4,681,264, 4,982,730, 5,046,486, 5,551,909, 6,199,773, 6,203,406, 6,454,871 and GB1008503. These devices operate on the basis of providing a liquid stream with a reduced boundary layer thickness employing fluid and air nozzle assemblies, a high velocity aerosol of at least partially frozen particles, and pulsed jets of liquid sprayed on to a metal surface in order to sweep away small particles. These devices, however, generally have complicated constructions, use very large quantities of liquid, and have been found to provide only a small improvement over non-pulsed spray devices.

Referring now to U.S. Pat. No. 5,730,806 entitled "Gas-liquid supersonic cleaning and cleaning verification spray system" to Caimi, et al. on Mar. 24, 1998, there is disclosed a gas-liquid cleaning spray system which employs one or more converging-diverging nozzles to accelerate a gas-liquid mixture to a supersonic velocity for cleaning various types of articles, such as mechanical, electrical and fluid components.

Referring now to U.S. Pat. No. 6,293,498 and U.S. Pat. No. 6,360,992 entitled "Hybrid deicing system and method of operation" to Stanko, et al. on Sep. 25, 2001 and Mar. 26, 2002 respectively, there is disclosed an invention which overcomes the disadvantage of the prior systems and produces a high velocity specially formed and constituted pressure aerodynamic stream system for efficiently and effectively removing ice from an aircraft.

Referring now to U.S. Pat. No. 5,100,412 entitled "Apparatus for making micro-abrasions, particularly on human tissue or on hides" to Rosso on Mar. 31, 1992 there is disclosed apparatus for making micro-abrasions, particularly on human tissue, which includes a handle having an aperture which is intended to be positioned on the surface to be treated, and a nipple device for the metered supply of reducing substances in a pneumatic carrier to the aperture of the handle. The supply device comprises only a vacuum source connected to the handle to draw the reducing substances towards the aperture of the handle. A collector device is provided for collecting the used substances for disposal.

Referring now to U.S. Pat. No. 5,207,234 entitled "Method for making micro-abrasions on human tissue" to Rosso on May 4, 1993, there is disclosed a method for making micro-abrasions on human tissue. The method includes placing a handle having an open chamber therein on human tissue to close the chamber, applying suction to the chamber to sealingly engage the periphery of the chamber with the human tissue and partially sucking the human tissue into said chamber. This induces the flow of air into the chamber by the removal of air from the chamber by suction while restricting entry of ambient air from the surrounding atmosphere into the chamber around the periphery of the chamber, entraining a reducing substance in said flow of air prior to entry of the flow of air into the chamber. This directs the reducing substance entering the chamber against the human tissue at an angle less than 90 degrees, entraining used reducing substances and abraded tissue in the flow of air being removed from the chamber by suction and collecting used reducing substances and abraded tissue in a manner to prevent reuse of the reducing substances during continued application of a vacuum to the chamber.

Referring now to U.S. Pat. No. 5,810,842 entitled "Equipment for microdermoabrasion through a flow of an air/reducing substances mix" to Di Fiore, et al. on Sep. 22, 1998, there is disclosed a device for microdermoabrasion using a flow of a mixture of air and reducing substances. The device comprises a casing with a vacuum pump and a compressor at an interior of the casing. The device further comprises a control footswitch for actuating the compressor, a mixing bulb and a collecting bulb at an exterior of the casing, and a handpiece extending between the mixing bulb and the collecting bulb. The mixing bulb contains a mixture of air and reducing substances.

Further, there have been developed a multiplicity of dental cleaning devices, which operate to clean teeth, cavities and spaces between the teeth. Some such devices also address the problem of gingivitis. Included amongst such devices are U.S. Pat. Nos. 5,013,241, 5,203,698, 5,273,428, 5,387,182, 5,667,483, 6,120,755, 6,224,378, 6,497,572 and DE19654098, FR2654331, FR2599244, DE3726349.

Referring now to Israel Patent No. 118801 entitled "Apparatus and Method for Cleansing Tissue" to M. Tavger on Dec. 16, 2001, there is disclosed apparatus employing liquid and gas as working fluids for cleansing living tissue, which includes: a container for a sterile liquid; a fluid delivery head having a liquid entry port and a gas entry port, fluid outlet apparatus, and valve apparatus located between the entry ports and the fluid outlet apparatus and for selectably permitting respective liquid and gas flows from the entry ports to the fluid outlet apparatus; liquid conduit apparatus extending between a liquid inlet located within the container and a liquid outlet connected to the liquid entry port of the delivery head; gas conduit apparatus extending between a gas inlet and a gas outlet, wherein the gas inlet is connected to a source of pressurized gas and the gas outlet is connected to the gas entry port of the delivery head, and wherein the gas conduit apparatus is connected to the container via an intermediate outlet port; and apparatus for selectably exposing the source of sterile liquid to a flow of pressurized gas flowing from the gas inlet to the gas outlet and into the gas entry port of the fluid delivery head, thereby to pump the sterile liquid along the liquid conduit apparatus, from the inlet to the outlet, and into the liquid entry port of the fluid delivery head, wherein the fluid outlet apparatus comprises a gas-liquid combining member arranged to receive the gas and liquid flows and to combine them into a gas-liquid outflow which is operative to exit the apparatus through the fluid outlet in the form of a sterile liquid mist suspended in a high velocity gas stream.

Referring now to Israel Patent No. 122016 entitled "Apparatus for Dermal Abrasion" to M. Tavger on Dec. 16, 2001, there is disclosed a method of dermal abrasion, which includes exposing a source of sterile liquid to a flow of pressurized gas, thereby causing a pumped supply thereof into a fluid delivery head; supplying the pressurized gas to the fluid delivery head; and combining the gas and liquid supplied to the delivery head; this fluid delivery head having a fluid outlet with a predetermined internal diameter, so as to provide a gas-liquid outflow in the form of a sterile liquid mist jet suspended in a high velocity gas stream; and exposing to the mist jet, at a preselected distance from the fluid outlet, a portion of the skin surface sought to be abraded, thereby separating therefrom at least a portion of the epidermis and removing therefrom the resulting tissue debris.

Many of the dermal abrasion and cleansing devices disclosed hereinabove have a specific drawback, when employed for tissue abrasion or skin peeling. The relatively high flow rate of liquid employed by the above-mentioned cleansing devices reduces the cleansing and scouring effect as a result of the development of a virtually stagnant boundary layer over the surface to be cleaned. There is a need in the art, notably in relation to dermal abrasion and to cleansing tissue surfaces or cavities, to avoid boundary layer formation during the cleansing process by utilizing a minimal flow of liquid.

SUMMARY OF THE INVENTION

The present invention aims to provide a device for the abrasion of tissue, using a relatively low rate of flow of cleansing liquid formed as a mist of droplets carried in a high velocity gas. The mist droplets are driven against the tissue surface, mass or cavity to be abraded at a very high velocity, thereby scouring the tissue surface. Further, the low rate of flow of liquid effectively ensures the formation of virtually no liquid boundary layer, thereby maximizing the abrading effect.

According to a preferred embodiment of the present invention there is provided a device for abrading tissue, which includes:
 a gas inlet port connected to a pressurized gas source;
 a liquid inlet port connected to a pressurized liquid source; and
  a mist jet delivery nozzle arrangement, which includes one or more gas discharge nozzles arranged to receive a flow of pressurized gas from the gas inlet port and configured to accelerate the flow of gas so as to discharge it at an elevated velocity, and further includes one or more liquid discharge nozzles arranged to receive a flow of liquid from the liquid inlet port and operative to discharge the flow of liquid into the elevated velocity flow of gas, thereby to similarly accelerate the velocity of the discharged liquid as a mist of accelerated droplets.

According to another preferred embodiment of the present invention there is provided a device for abrading tissue, which includes a gas inlet port connected to a pressurized gas source, a liquid inlet port connected to a pressurized liquid source, a mist jet delivery nozzle arrangement and a suction nozzle arrangement. The device further comprises suction means, which includes a suction conduit disposed in operative association with respect to the mist jet delivery nozzle arrangement and including one or more suction ports. The device, additionally, comprises an atmospheric air inlet conduit having at least one air inlet port disposed in operative association with respect to the suction conduit and to the mist jet delivery nozzle arrangement, and moreover means for applying a suction force to the suction conduit, thereby to cause suctioning from one or more suction ports of liquid and abraded tissue particles in the vicinity of the mist jet delivery nozzle arrangement.

In accordance with an embodiment of the present invention, the device further comprises suction means, which includes a suction conduit disposed in operative association with respect to the mist jet delivery nozzle arrangement and including one or more suction ports. The device additionally comprises an atmospheric air inlet conduit having one or more air inlet ports disposed in operative association with respect to the suction conduit and to the mist jet delivery nozzle arrangement, and moreover means for applying a suction force to the suction conduit, thereby to cause suctioning from the one or more suction ports of liquid and abraded tissue particles in the vicinity of the mist jet delivery nozzle arrangement.

In accordance with another embodiment of the present invention, gas is supplied from the pressurized gas source at a pressure in the range of 40-150 p.s.i. and liquid is supplied from the pressurized liquid source at a pressure in the range of 0 to 5 p.s.i.

In accordance with one other embodiment of the present invention, the gas supplied from the pressurized gas source includes one or more of air, oxygen, carbon dioxide and nitrogen.

In accordance with a further embodiment of the present invention, the gas discharged from the one or more gas discharge nozzles is accelerated to a velocity in the range of sub-sonic to supersonic velocity.

In accordance with an additional embodiment of the present invention, the mist jet delivery nozzle arrangement includes at least two gas discharge nozzles or at least two liquid discharge nozzles.

In accordance with one other embodiment of the present invention, the one or more liquid discharge nozzles are disposed substantially concentric and within the one or more gas discharge nozzles.

In accordance with an additional embodiment of the present invention, the one or more gas discharge nozzles are devices configured to have a converging portion, a throat portion and a diverging portion.

In accordance with an embodiment of the present invention, the device is configured to be used while being held in one hand.

In accordance with one other embodiment of the present invention, the flow of gas entering the one or more gas discharge nozzles is at a pressure of a first magnitude, and the one or more gas discharge nozzles are operative to cause a pressure drop in the gas flow therethrough such that the pressure of the gas discharged from the one or more gas discharge nozzles is of a second magnitude, wherein the first magnitude is at least twice the second magnitude, so as to cause a shock wave in the gas and liquid flow downstream of the one or more gas discharge nozzles and the one or more liquid discharge nozzles so as to cause atomizing of the liquid discharged from the one or more liquid discharge nozzles into a high velocity mist of droplets, thereby to form a mist of droplets suspended in the flow of discharged high velocity gas.

According to another preferred embodiment of the present invention, there is provided a system for abrading tissue. The system includes a pressurized gas source, a pressurized liquid source and a device which includes:
- a gas inlet port connected to the pressurized gas source;
- a liquid inlet port connected to the pressurized liquid source; and
- a mist jet delivery nozzle arrangement including one or more gas discharge nozzles arranged to receive a flow of pressurized gas from the gas inlet port and configured to accelerate the flow of gas so as to discharge it at an elevated velocity. The device further includes one or more liquid discharge nozzles arranged to receive a flow of liquid from the liquid inlet port and operative to discharge the flow of liquid into the elevated velocity flow of gas, thereby to similarly accelerate the velocity of the discharged liquid as a mist of accelerated droplets.

In accordance with an embodiment of the present invention the system further includes a suction conduit disposed in operative association with respect to the mist jet delivery nozzle arrangement and including one or more suction ports and, also, an atmospheric air inlet conduit having one or more air inlet ports disposed in operative association with respect to the suction conduit and to the mist jet delivery nozzle arrangement. The system additionally includes means for applying a suction force to the suction conduit, thereby to cause suctioning from one or more suction ports of liquid and abraded tissue particles in the vicinity of the mist jet delivery nozzle arrangement.

In accordance with another embodiment of the present invention, gas is supplied from the pressurized gas source at a pressure in the range of 40-150 p.s.i. and liquid is supplied from the pressurized liquid source at a pressure in the range of 0 to 5 p.s.i.

In accordance with one other embodiment of the present invention, the gas supplied from the pressurized gas source includes one or more of air, oxygen, carbon dioxide and nitrogen.

In accordance with another embodiment of the present invention, the gas discharged from the one or more gas discharge nozzles is accelerated to a velocity in the range of sub-sonic to supersonic velocity.

In accordance with an added embodiment of the present invention, the mist jet delivery nozzle arrangement includes at least two gas discharge nozzles. In accordance with another embodiment of the present invention, the mist jet delivery nozzle arrangement includes at least two liquid discharge nozzles. In accordance with an additional embodiment of the present invention, the one or more liquid discharge nozzles are disposed substantially concentric and within the one or more gas discharge nozzles.

In accordance with one other embodiment of the present invention, the one or more gas discharge nozzles are devices each configured to have a converging portion, a throat portion and a diverging portion.

In accordance with one other embodiment of the present invention, the device is configured to be used while being held in one hand.

In accordance with a further embodiment of the present invention, the flow of gas entering the one or more gas discharge nozzles is at a pressure of a first magnitude, and the one or more gas discharge nozzles are operative to cause a pressure drop in the gas flow therethrough such that the pressure of the gas discharged from the one or more gas discharge nozzles is of a second magnitude, wherein the first magnitude is at least twice the second magnitude, so as to cause a shock wave in the gas and liquid flow downstream of the one or more gas discharge nozzles and the one or more liquid discharge nozzles so as to cause atomizing of the liquid discharged from the one or more liquid discharge nozzles into a high velocity mist of droplets, thereby to form a mist of droplets suspended in the flow of discharged high velocity gas.

Furthermore, there is provided a method for abrading tissue by application of a high velocity liquid-gas mist thereto. The method includes a step of accelerating a flow of gas through one or more gas nozzles so as to provide a gas discharge flow at an elevated velocity, another step of introducing into the elevated velocity gas discharge flow a flow of liquid, thereby to fragment the liquid into a mist of droplets, and to accelerate the mist to an accelerated velocity similar to the velocity of the gas discharge flow, and a further step of exposing a desired tissue mass to the accelerated droplet mist.

In accordance with an embodiment of the present invention, the method includes an additional step of applying a suction force to a suction conduit, thereby to cause suctioning from at least one suction port of liquid and abraded tissue particles in the vicinity of the gas and mist discharge flow.

In accordance with one other embodiment of the present invention, the step of accelerating a flow of gas includes accelerating the flow of gas to a velocity in the range of sub-sonic to supersonic velocity.

In accordance with another embodiment of the present invention, the step of accelerating a flow of gas includes accelerating the flow of gas to a velocity in the range of sonic to supersonic velocity.

In accordance with an additional embodiment of the present invention, the step of accelerating a flow of gas includes accelerating a gas selected from the group of gases including one or more of air, oxygen, nitrogen and carbon dioxide.

In accordance with a further embodiment of the present invention, the step of introducing into the elevated velocity gas discharge flow a flow of liquid, includes the flow of gas entering the one or more gas discharge nozzles being at a pressure of a first magnitude, and the one or more gas discharge nozzles being operative to cause a pressure drop in the gas flow therethrough such that the pressure of the gas discharged from the one or more gas discharge nozzles is of a second magnitude, wherein the first magnitude is at least twice the second magnitude, thereby causing a shock wave in the gas and liquid flow downstream of the one or more gas discharge nozzles and the one or more liquid discharge nozzles so as to cause atomizing of the liquid discharged from the one or more liquid discharge nozzles into a high velocity mist of droplets, thereby forming a mist of droplets suspended in the flow of discharged high velocity gas.

In accordance with one other embodiment of the present invention, the step of exposing a desired tissue mass to the accelerated droplet mist includes holding the device in one hand.

In accordance with an embodiment of the present invention, the step of exposing a desired tissue mass includes cleansing the tissue mass thereby to remove contaminants from the tissue mass.

In accordance with another embodiment of the present invention, the step of exposing a desired tissue mass includes dispersing accumulated liquid from the tissue mass by the flow of high velocity gas.

In accordance with a further embodiment of the present invention, the step of exposing a desired tissue mass includes cleansing away and destroying residual anaerobic organisms using a sterile liquid mist in a flow of oxygen gas.

BRIEF DESCRIPTION OF THE DRAWINGS

The present invention will be more fully understood and its features and advantages will become apparent to those skilled in the art by reference to the ensuing description, taken in conjunction with the accompanying drawings, in which.

DETAILED DESCRIPTION OF THE INVENTION

The present invention relates to a device for abrading tissue by directing thereat a liquid-gas mist of droplets at a high velocity generally within the range of sub-sonic to supersonic. To achieve this, gas is discharged from a converging-diverging gas nozzle configured to accelerate the flow of gas so as to discharge it at an elevated velocity. A low rate of flow of liquid is discharged into the elevated velocity flow of gas, thereby to similarly accelerate the velocity of the discharged liquid as a mist of accelerated droplets. The volumetric rate of flow of liquid from the device is relatively low, thereby minimizing the formation of a virtually stagnant liquid boundary layer on the surface of the tissue to be abraded.

Figure 1:
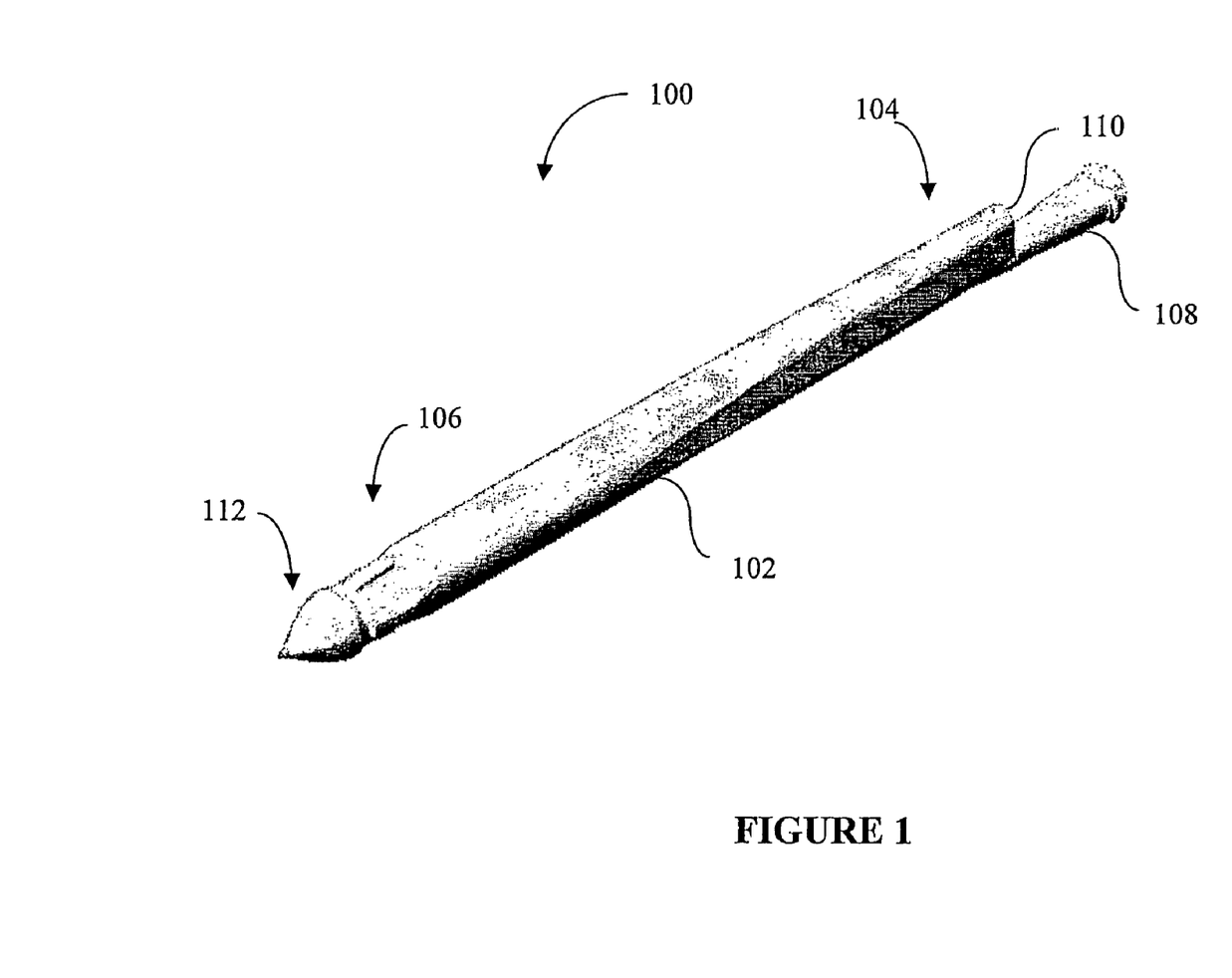
FIG. 1 is a perspective view of a tissue abrasion device, constructed and operative constructed and operative in accordance with a preferred embodiment of the present invention.
Figure 2:
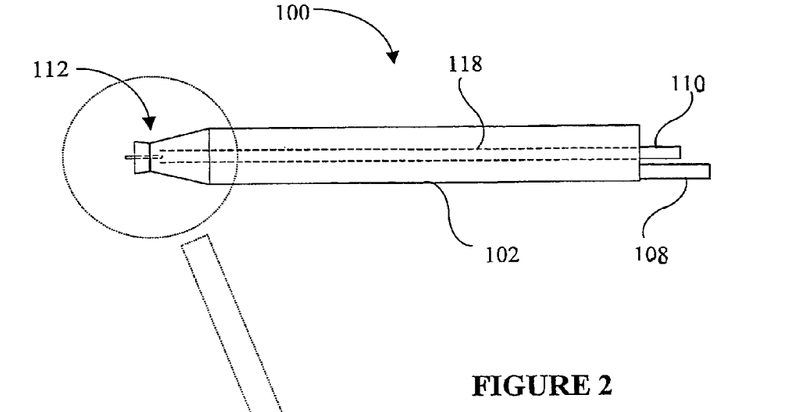
FIG. 2 is a schematic side view of the device of FIG. 1.
Figure 3:
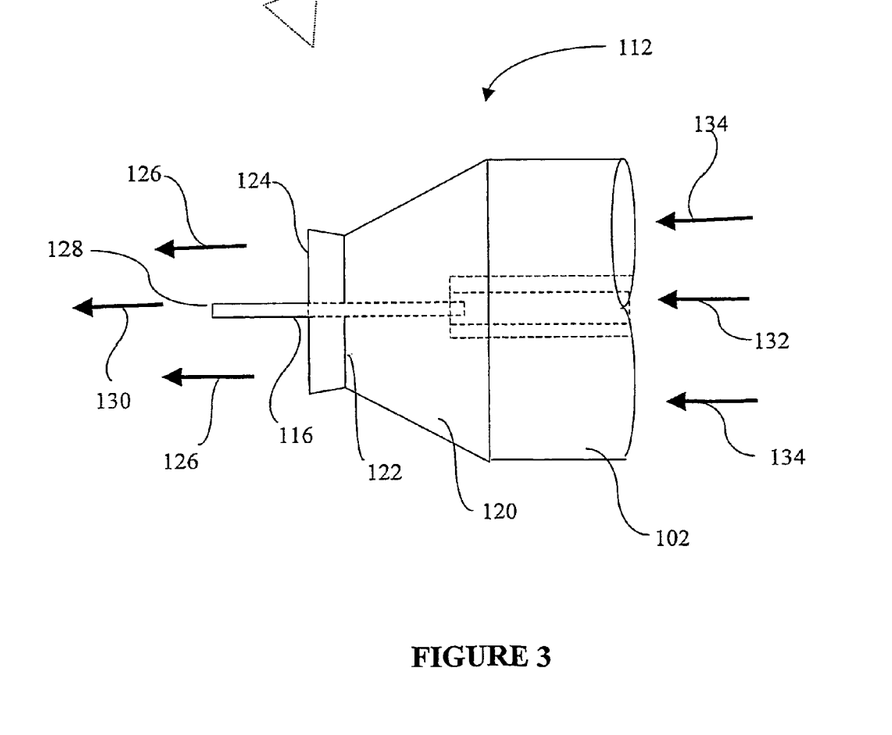
FIGS. 3 and 4 are enlarged schematic and graphical representations, respectively, of a delivery nozzle arrangement of the device seen in FIGS. 1 and 2.
Figure 4:
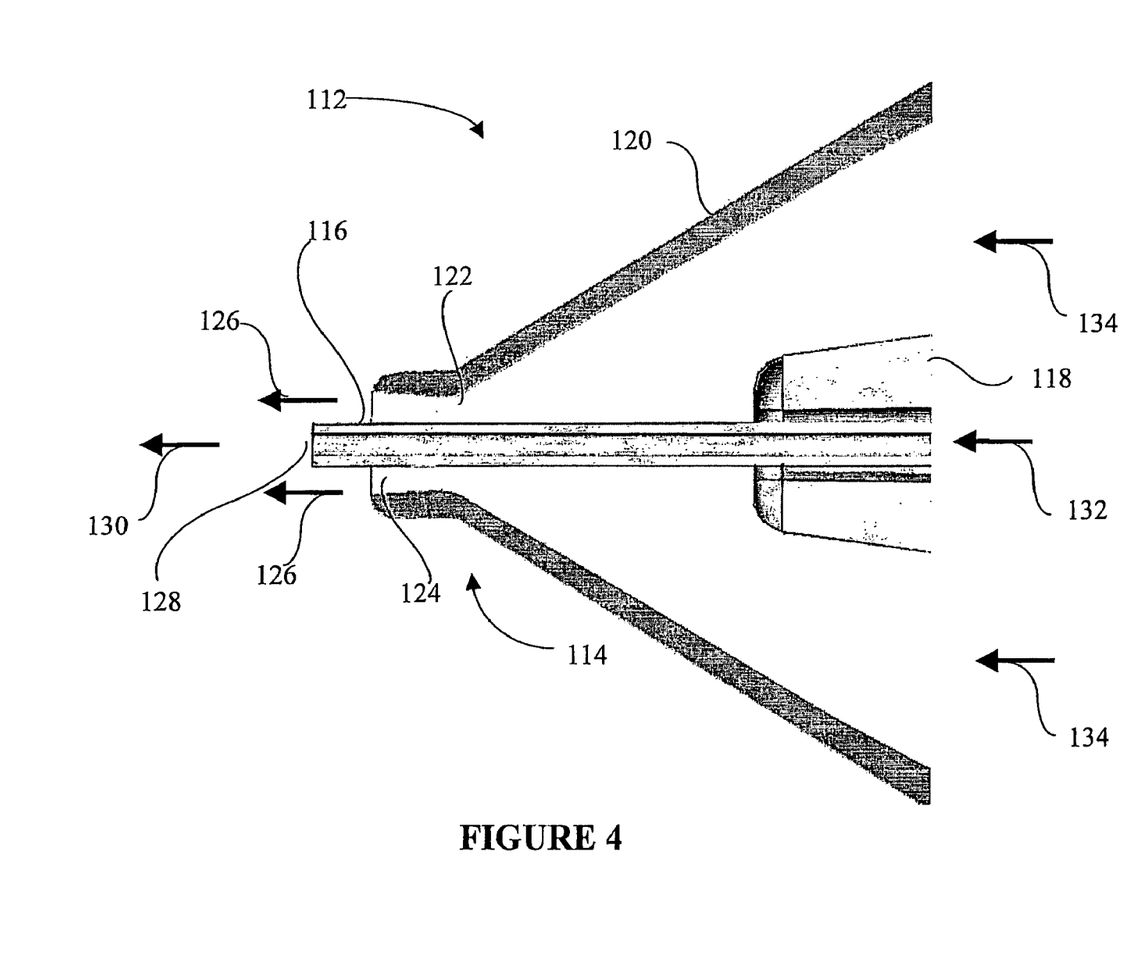
Figure 5:
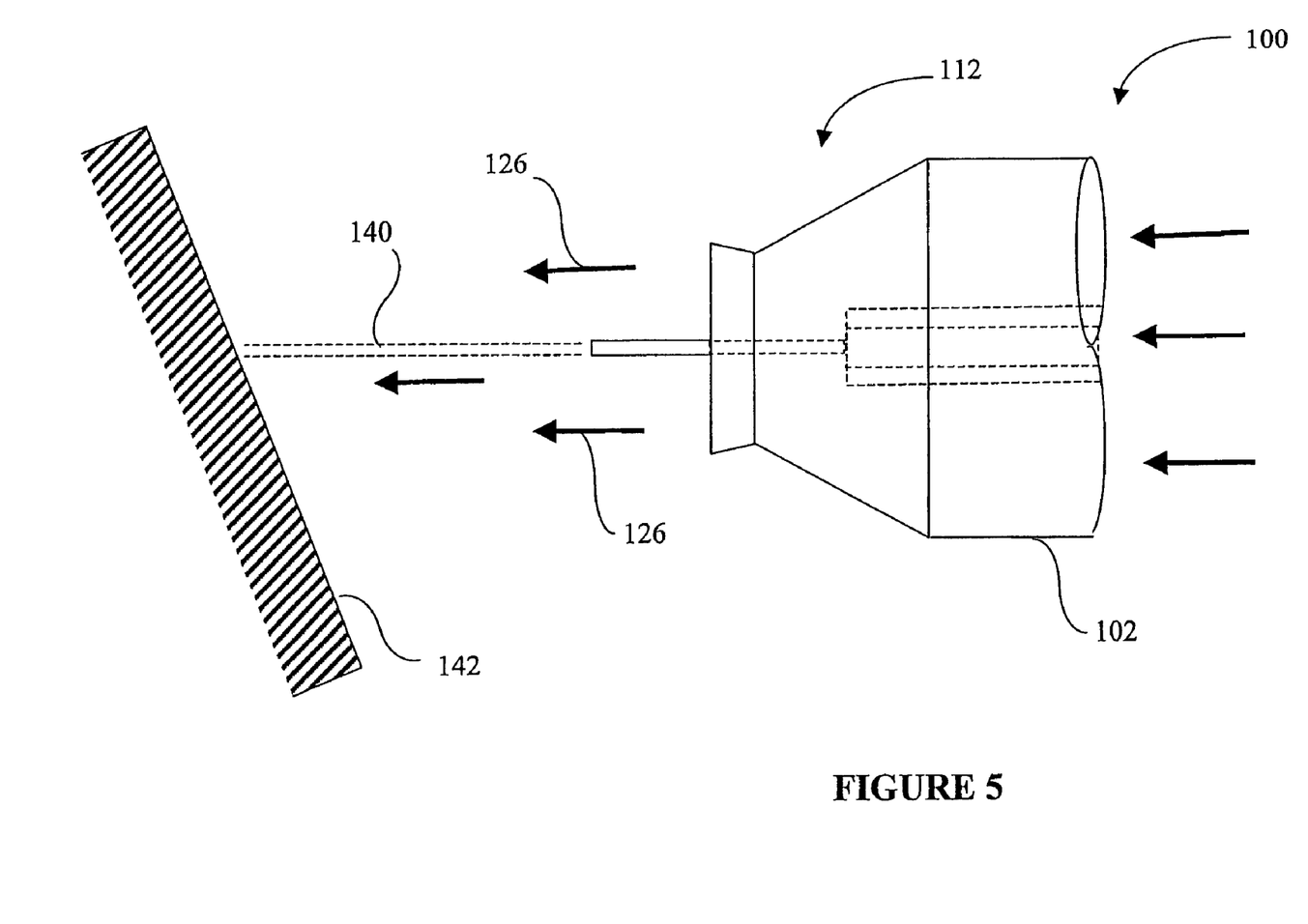
FIG. 5 is a schematic view of a flow of mist droplets discharging from the delivery nozzle arrangement as seen in FIG. 4 against a surface to be abraded.

With reference to FIGS. 1 and 2, there is seen, according to a preferred embodiment of the present invention, a device referenced generally 100 for applying a high velocity liquid-gas mist to tissue thereby to cause abrasion thereof. Alternatively, the velocity of the mist may be regulated so as to merely provide cleansing or debradement of the tissue. Device 100 includes a housing portion referenced 102 having a generally tubular configuration, and having proximal and distal ends, referenced generally 104 and 106 respectively. A gas inlet port referenced 108 and a liquid inlet port referenced 110 are provided at proximal end 104, and a mist jet delivery nozzle arrangement referenced generally 112, is provided at distal end 106.

Referring now to FIGS. 3 and 4 in conjunction with FIG. 2, there are seen schematic cross-sectional views of nozzle arrangement 112 of device 100. Nozzle arrangement 112 includes a gas discharge nozzle referenced generally 114 and, disposed generally concentrically there-within, is a liquid discharge nozzle referenced 116. Liquid inlet port 110 is connected in fluid flow communication with liquid discharge nozzle 116 by means of a liquid communication tube referenced 118, disposed generally concentrically within tubular housing portion 102.

Pressurized gas supplied from a pressurized gas source (not shown) enters device 100 through gas inlet port 108 and passes along and within tubular housing portion 102 as indicated by arrows 134, so as to discharge through gas discharge nozzle 114. Gas discharge nozzle 114 is generally configured having, in flow succession, a converging portion referenced 120, a throat portion referenced 122 and a diverging discharge portion referenced 124. The pressurized gas discharging from nozzle 114, as indicated by arrows 126, undergoes a rapid and substantial reduction in pressure to atmospheric pressure and a substantial acceleration to a high velocity, within the range of subsonic to supersonic velocity and specifically to a supersonic velocity. Gas discharge nozzle 114 is configured such that the discharging gas has a cone angle of less than 10 degrees, that is, providing a substantially parallel gas flow.

Liquid from a pressurized liquid source (not shown) enters device 100 through liquid inlet port 110 and passes, as indicated by arrow 132, through liquid communication tube 118. In turn, at distal end 106, liquid is discharged through an opening referenced 128 in the distal end of liquid discharge nozzle 116 into the discharging flow 126 of gas, the liquid flow being indicated by arrow 130.

It will be appreciated by persons skilled in the art that, as the pressurized discharging gas emerges 126 from gas discharge nozzle 114 into the atmosphere, it undergoes a rapid drop in pressure to atmospheric pressure. The sudden pressure drop results in a substantial acceleration of the velocity of the discharging gas flow that approximates or even exceeds the velocity of sound and the production of a shock wave. The effect of the shock wave is to atomize the liquid discharging from liquid discharge nozzle 116 into the flow of gas as a mist of liquid droplets 130, such that there is obtained a relatively narrow jet of liquid droplets in a high velocity gas flow 126.

Further, by way of example, the proportion of liquid flow to gas flow is extremely low due to the relatively high gas pressure of about 100 p.s.i. and low liquid pressure of about 2 p.s.i., as well as the relatively large internal diameter of gas discharge nozzle 114 (about 0.8 mm) compared to a small internal diameter (about 0.09 mm) of liquid discharge nozzle 130. Consequently, little liquid tends to accumulate at the site to be abraded or scoured. Furthermore, the relatively high gas flow has the effect of dispersing any accumulated liquid. When using a jet utilizing only liquid for cleansing, the liquid tends to accumulate on the tissue surface resulting in formation of a virtually stagnant liquid boundary layer close to and in contact with the surface, thereby reducing the effectiveness of cleansing.

Referring now to FIG. 5, there is seen a high velocity flow of mist droplets referenced 140 discharging, in a high velocity gas flow 126, from nozzle arrangement 112 against a tissue surface referenced 142 to be abraded or scoured. Device 100 is held in the hand of a user by housing portion 102.

Figure 6:
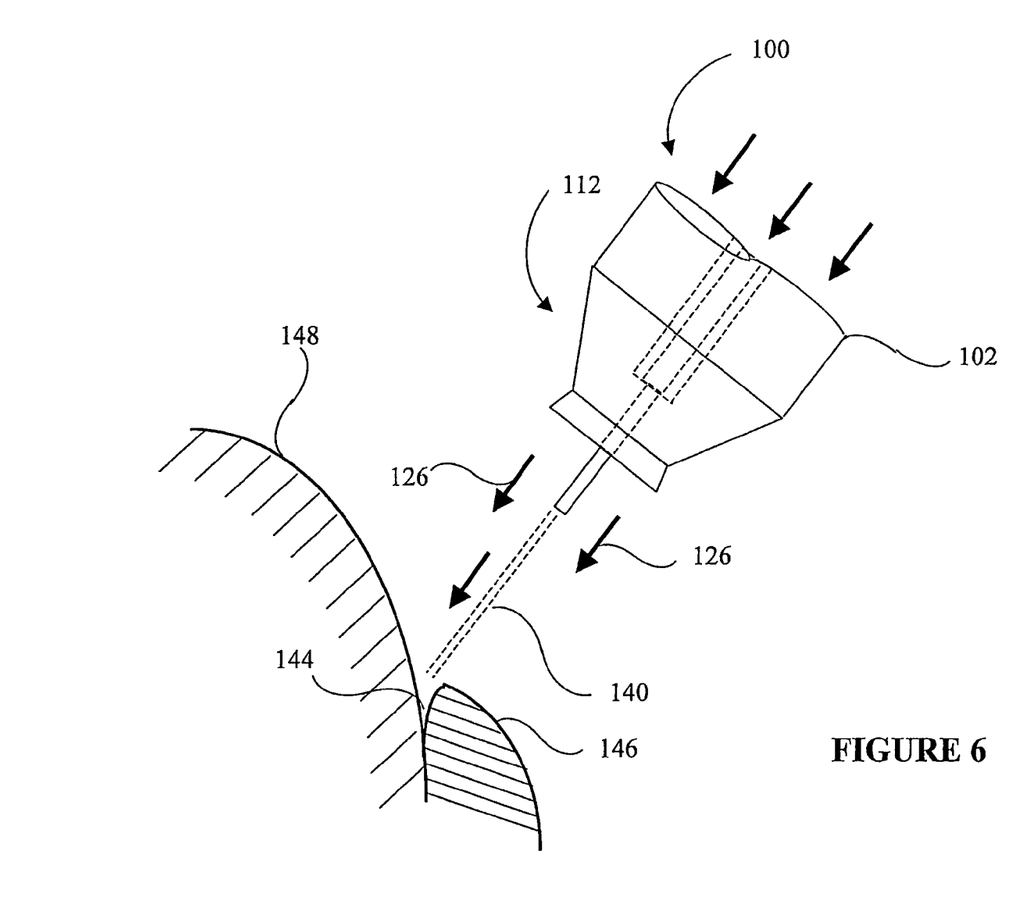
FIG. 6 is a schematic view of a flow of mist droplets discharging from the delivery nozzle arrangement seen in FIG. 4, into a periodontal pocket.

Referring now to FIG. 6, there is seen a flow of mist droplets 140 discharging, in a high velocity gas flow 126, from nozzle arrangement 112 of device 100 into a periodontal pocket referenced 144 disposed between a gum referenced 146 and a tooth wall referenced 148. Device 100 is held in the hand of a user by housing portion 102. This procedure is especially effective for scouring or cleansing periodontal pockets, subsequent to a dental descaling treatment, so as to remove plaque and calculus debris as well as bacteria and the toxins produced by the bacteria, which otherwise lead to mechanical irritation and inflammation of the gingiva.

Figure 7:
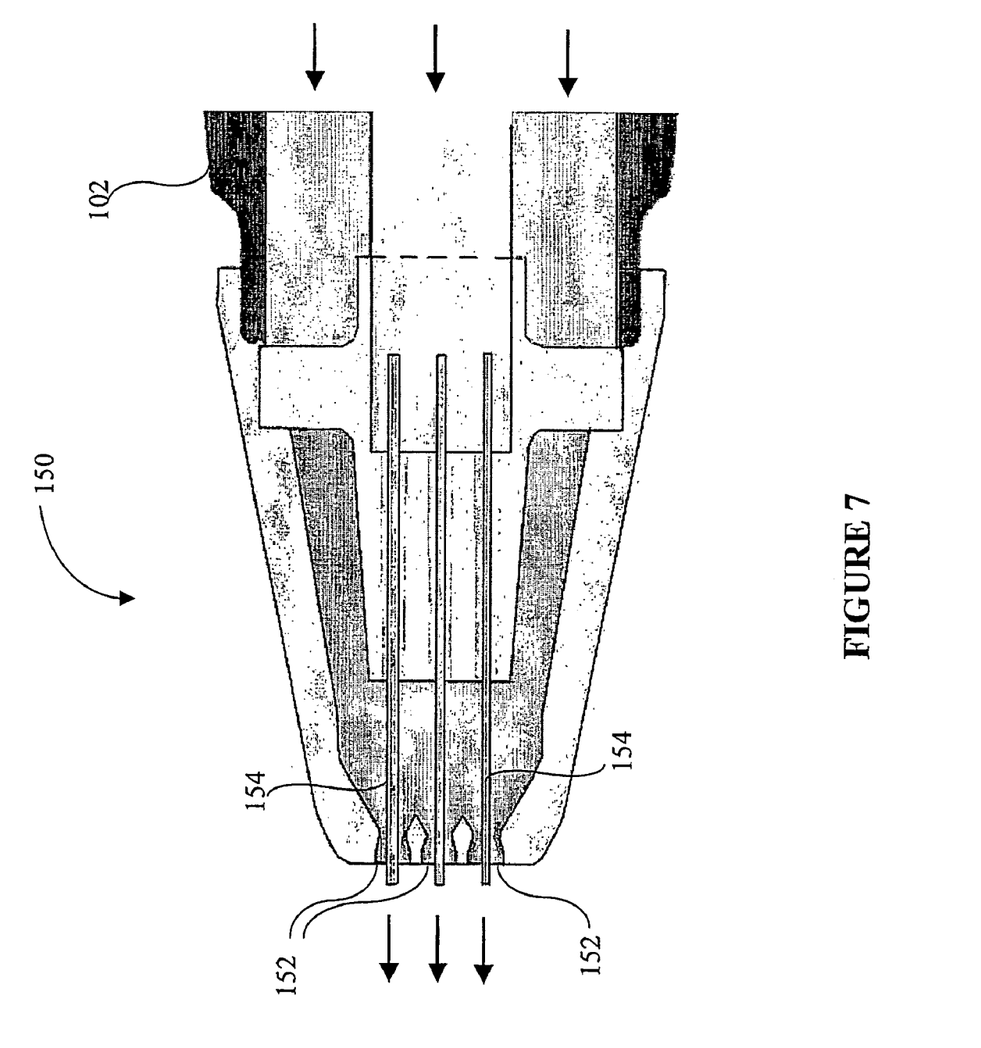
FIG. 7 is a schematic view of a nozzle arrangement, constructed and operative in accordance with an alternative embodiment of the present invention, having multiple gas and liquid discharge nozzles.

Referring now to FIG. 7, there is seen, according to an alternative embodiment of the present invention, a cross-sectional view of a device (not shown) having a housing portion 102 and a multiple nozzle arrangement referenced generally 150. Nozzle arrangement 150 is configured having multiple gas discharge nozzles referenced 152 and multiple liquid discharge nozzles referenced 154 disposed generally concentrically within each gas nozzle 152 and projecting there-beyond. Such a multiple nozzle arrangement 150 facilitates expanding the rate of tissue abrasion or skin peeling, or debradement, in the event that the system is used for this purpose.

Figure 8:
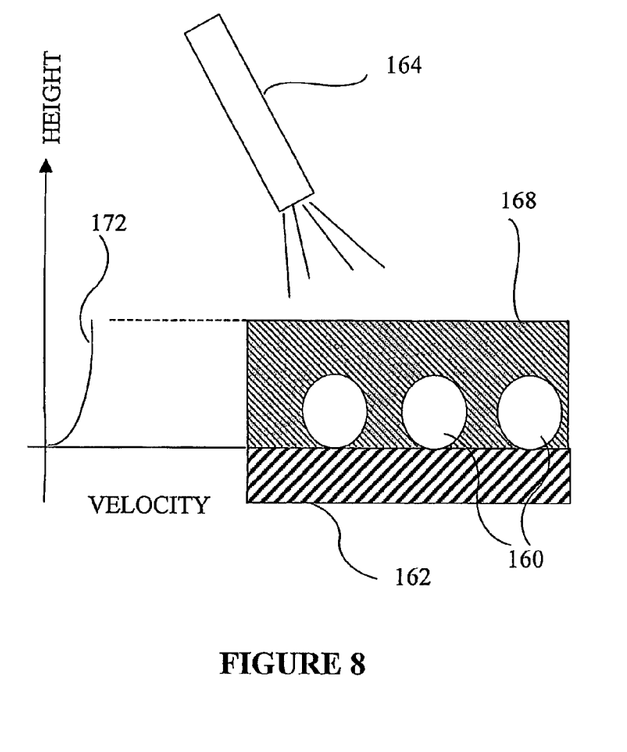
FIGS. 8 and 9 illustrate the effect of a boundary layer formed on a surface being abraded.
Figure 9:
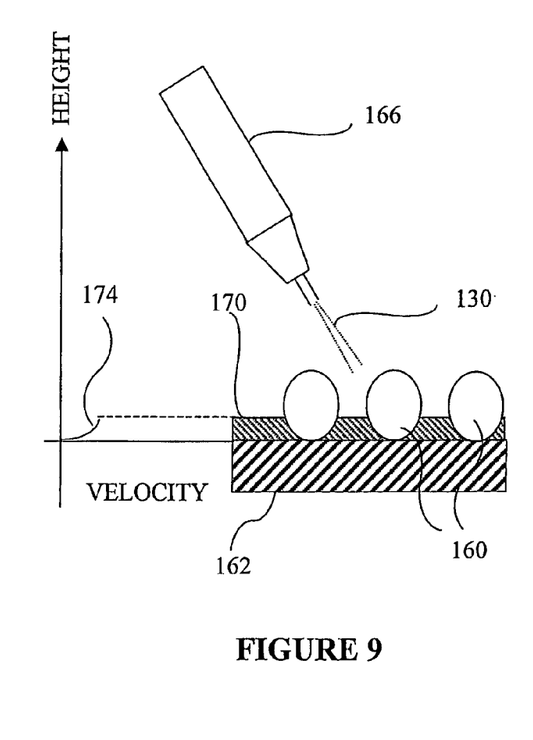

Referring now to FIGS. 8 and 9, there are illustrated the relative effects of scouring or cleansing contaminants or debris, including dermal debris, referenced 160 from a tissue surface referenced 162, using a liquid spray nozzle referenced 164 (in FIG. 8) compared to that using a high velocity liquid-gas mist device referenced 166 (in FIG. 9). Spray nozzle 164 causes a build up of a virtually stagnant liquid boundary layer referenced 168, resulting in a reduction of the effectiveness of the scouring or cleansing procedure. Dispenser 166 utilizes a relatively small amount of liquid as high velocity mist droplets referenced 130 in a high velocity gas flow to carry out the scouring or debradement procedure. In addition, most of the accumulated liquid referenced 170 is displaced from surface 162 and debris 160 by impingement of the high velocity gas flow. The velocity profiles referenced 172 and 174, illustrated in FIGS. 8 and 9 respectively, indicate the relative resistance to scouring presented by the respective boundary layers 168 and 170.

In addition, the wetting of the debris or contaminants in this way, even by microscopic droplets, causes a substantial increase in their aerodynamic resistance to scouring, such that a substantial force of bombardment by the combined high velocity liquid droplets and gas flow is needed to debrade or separate debris from the tissue surface and carry away debraded particles in the droplet stream. The increase in the aerodynamic resistance of the particles is caused by the wetting of these particles by liquid droplets, on the one hand, and by the absence, on the tissue surface of a stable liquid boundary layer, on the other hand. Accordingly, as none of the contaminant particulate matter is protected by a stable boundary layer of a liquid stream, particles are exposed to removal by the gas-liquid droplet stream.

In order to further reduce the aerodynamic resistance to cleansing or abrading of tissue caused by accumulated water or tissue debris, there is substantial advantage to continuous physical removal of such accumulated material.

Figure 10:
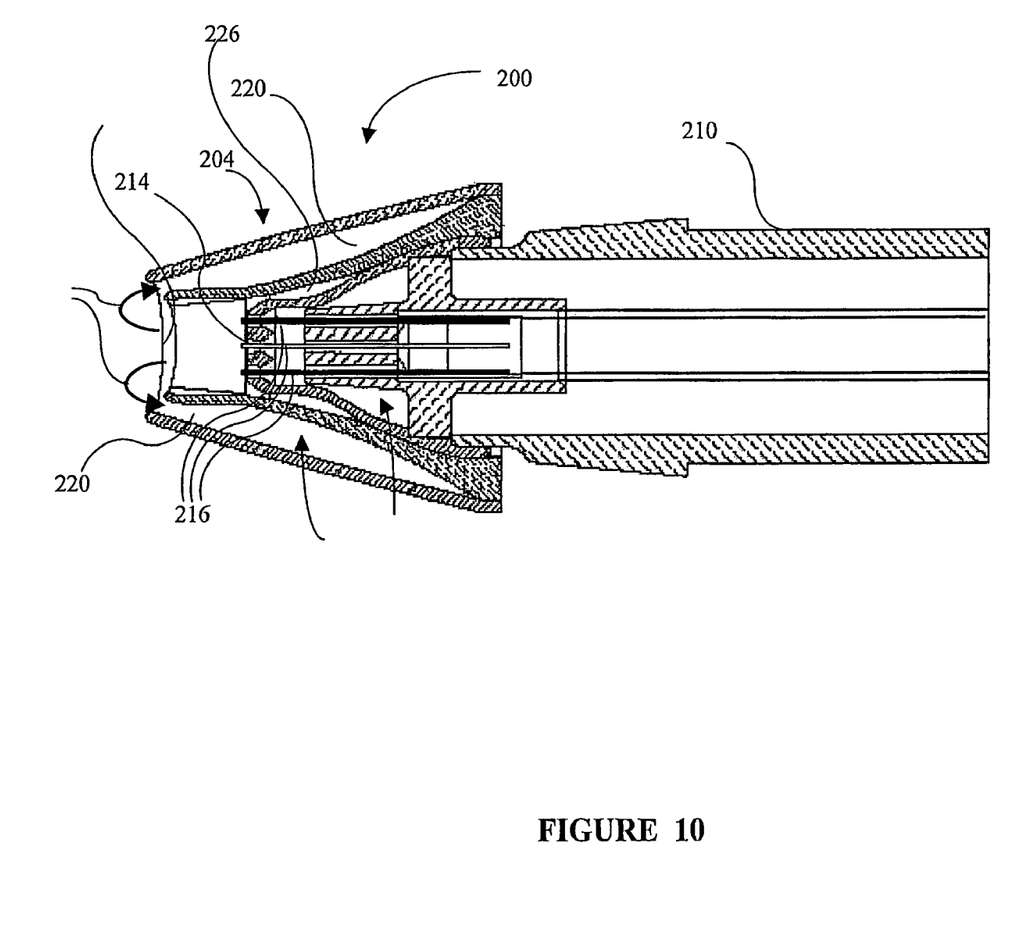
FIG. 10 is a cross-sectional partial plan view of a tissue abrasion device including a suction means in accordance with another embodiment of the present invention.
Figure 11:
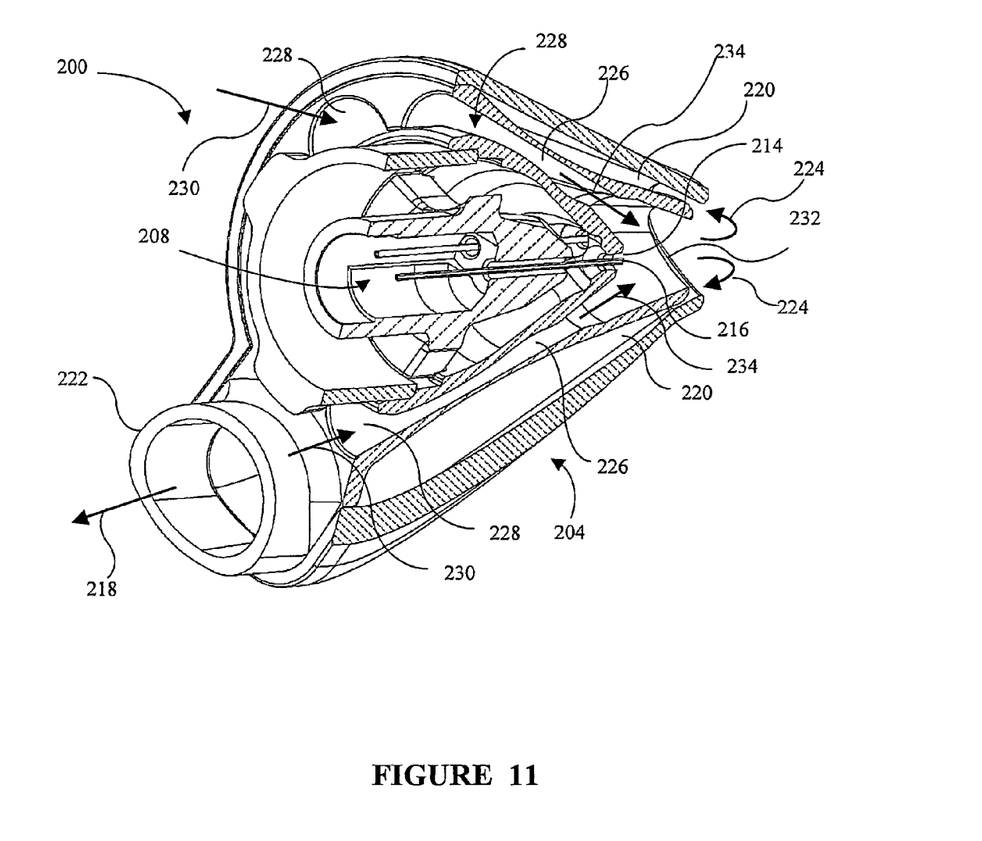
FIG. 11 is a perspective cut-away partial view of the tissue abrasion device including a suction means.
Figure 12:
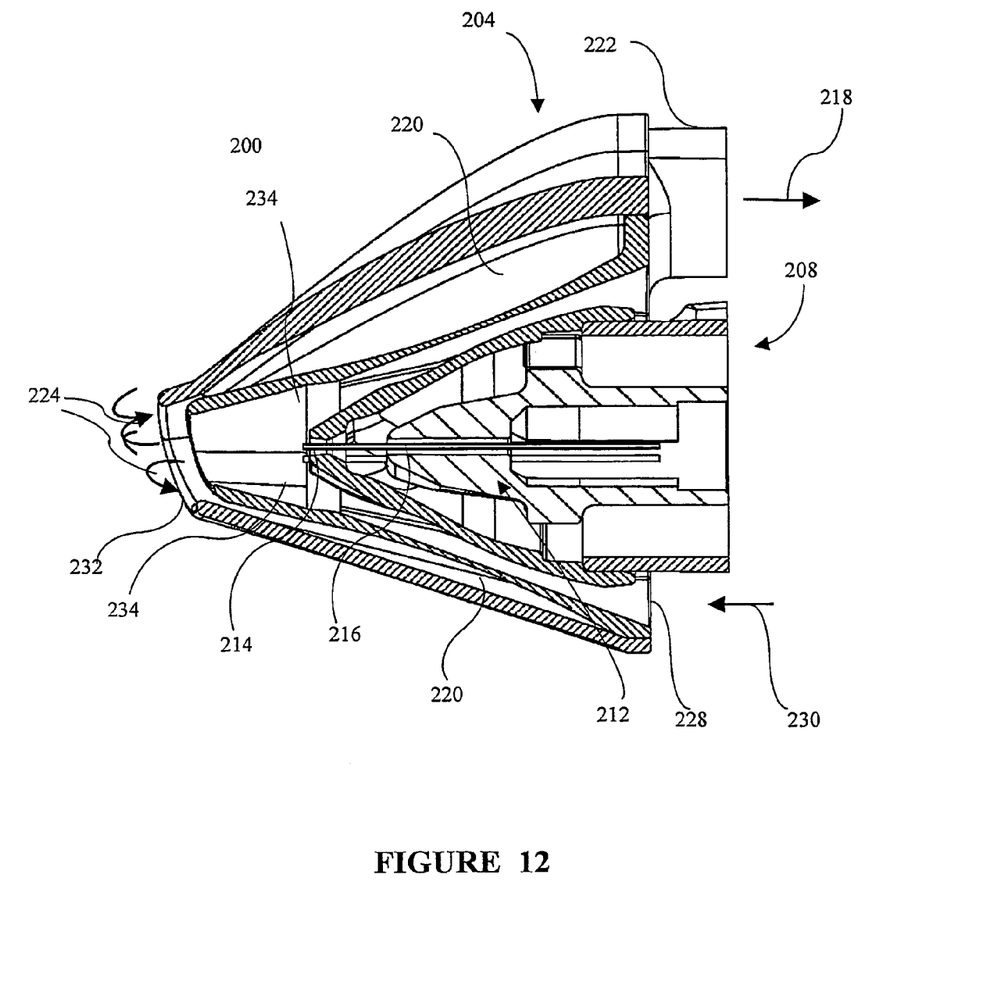
FIG. 12 is a cross-sectional partial elevation view of a tissue abrasion device including a suction means.

Referring now to FIGS. 10, 11 and 12, in accordance with an additional embodiment of the present invention, there is seen a device referenced generally 200 for applying a high velocity liquid-gas mist to tissue thereby to cause abrasion thereof and including a suction means generally referenced 204 disposed about mist jet delivery nozzle arrangement generally referenced 208.

Mist jet delivery nozzle arrangement 208 includes a housing portion 210 and a multiple nozzle arrangement referenced generally 212. Nozzle arrangement 212 is configured having multiple gas discharge nozzles referenced 214 and multiple liquid discharge nozzles referenced 216 disposed generally concentrically within each gas nozzle 214 and projecting there-beyond. Such a multiple nozzle arrangement 212 facilitates expanding the rate of tissue abrasion or skin peeling, or debradement, in the event that the system is used for this purpose.

Suction means 204 comprises two conduits or chambers, generally disposed coaxially about and in operative association with mist jet delivery nozzle arrangement 208. A vacuum or suction, as indicated by arrow 218, is applied to the outer suction conduit or chamber referenced 220 through a suction port referenced 222, so as to draw liquid, gas and abraded tissue particles or debris from the tissue surface as indicated by arrows 224 The inner atmospheric air conduit or chamber referenced 226 serves to permit atmospheric air to be drawn through inlet ports referenced 228 as indicated by arrows 230.

Device 200 is caused to operate for tissue abrasion or cleansing by discharging pressurized air through gas discharge nozzles 214 and discharging liquid from liquid discharge nozzles 216 into the gas stream. Device 200 is positioned in close contact with the tissue to be cleansed or abraded such that outer edge referenced 232 of suction chamber 220 comes into close contact with the tissue surface.

Suction from suction chamber 220 as indicated by arrows 224 is counterbalanced by atmospheric air being drawn into inlet ports 228 as indicated by arrows 230, through atmospheric air chamber 226 as indicated by arrows 234 and into suction chamber 220, as indicated by arrows 224. Thereafter, air together with any liquid and tissue debris is drawn away through suction chamber 220 and exits suction port 222 as indicated by arrow 218, for separation and disposal.

It will be appreciated by persons skilled in the art that the present invention is not limited by the drawings and description hereinabove presented. Rather, the invention is defined solely by the claims that follow.

The invention claimed is:

1. A device for abrading tissue having a distal end and a proximal end, which includes:
   a) a gas inlet port connected to a pressurized gas source;
   b) a liquid inlet port connected to a pressurized liquid source; and
   c) a mist jet delivery nozzle arrangement including
      i) at least one gas discharge nozzle arranged to receive a flow of pressurized gas from said gas inlet port and configured to accelerate the flow of gas so as to discharge it into the atmosphere at an elevated velocity at said distal end of said device so that the gas flow undergoes a rapid and substantial reduction in pressure to atmospheric pressure; and
      ii) at least one liquid discharge nozzle arranged to receive a flow of liquid from said liquid inlet port and configured and operative to discharge the flow of liquid at a point past said distal end of said device into the elevated velocity flow of gas, thereby to similarly accelerate a velocity of the discharged liquid as a mist of accelerated droplets.

2. A device in accordance with claim 1, which further includes suction means which includes a) a suction conduit disposed in operative association with respect to said mist jet delivery nozzle arrangement and including at least one suction port;

b) an atmospheric air inlet conduit having at least one air inlet port disposed in operative association with respect to said suction conduit and to said mist jet delivery nozzle arrangement; and c) means for applying a suction force to said suction conduit, thereby to cause suctioning from said at least one suction port of liquid and abraded tissue particles in a vicinity of said mist jet delivery nozzle arrangement.

3. A device in accordance with claim 1, wherein gas is supplied from the pressurized gas source at a pressure in the range of 40-150 p.s.i.

4. A device in accordance with claim 1, wherein liquid is supplied from the pressurized liquid source at a pressure in the range of 1 to 5 p.s.i.

5. A device in accordance with claim 1, wherein the gas supplied from the pressurized gas source includes at least one gas selected from: air, oxygen, carbon dioxide and nitrogen.

6. A device in accordance with claim 1, wherein gas discharged from said at least one gas discharge nozzle is accelerated to a velocity in the range of sub-sonic to supersonic velocity.

7. A device in accordance with claim 1, wherein said mist jet delivery nozzle arrangement includes at least two gas discharge nozzles.

8. A device in accordance with claim 1, wherein said mist jet delivery nozzle arrangement includes at least two liquid discharge nozzles.

9. A device in accordance with claim 1, wherein said at least one gas discharge nozzle is a device configured to have a converging portion, a throat portion and a diverging portion.

10. A device according to claim 9, wherein said at least one gas discharge nozzle is configured such that discharging gas has a cone angle of less than 10 degrees, thereby providing a substantially parallel gas flow.

11. A device in accordance with claim 1, wherein the flow of gas entering said at least one gas discharge nozzle is at a pressure of a first magnitude, and said at least one gas discharge nozzle is operative to cause a pressure drop in the flow of gas therethrough such that the pressure of the gas discharged from said at least one gas discharge nozzle is of a second magnitude, wherein the first magnitude is at least twice the second magnitude, so as to cause a shock wave in the flow of gas and the flow of liquid downstream of said at least one gas discharge nozzle and said at least one liquid discharge nozzle so as to cause atomizing of the liquid discharged from said at least one liquid discharge nozzle into a high velocity mist of droplets, thereby to form the mist of accelerated droplets suspended in the flow of discharged elevated velocity gas.

12. A system for abrading tissue, which includes:

a) a pressurized gas source;

b) a pressurized liquid source; and c) a device having a distal end and a proximal end which includes:

i) a gas inlet port connected to said pressurized gas source;

ii) a liquid inlet port connected to said pressurized liquid source; and iii) a mist jet delivery nozzle arrangement including 1) at least one gas discharge nozzle arranged to receive a flow of pressurized gas from said gas inlet port and configured to accelerate the flow of gas so as to discharge it into the atmosphere at an elevated velocity at the distal end of said device so that the gas flow undergoes a rapid and substantial reduction in pressure to atmospheric pressure; and 2) at least one liquid discharge nozzle arranged to receive a flow of liquid from said liquid inlet port and configured and operative to discharge the flow of liquid at a point past said distal end of said device into the elevated velocity flow of gas, thereby to similarly accelerate the velocity of the discharged liquid as a mist of accelerated droplets.

13. The system according to claim 12, wherein said system further includes a) a suction conduit disposed in operative association with respect to said mist jet delivery nozzle arrangement and including at least one suction port;

b) an atmospheric air inlet conduit having at least one air inlet port disposed in operative association with respect to said suction conduit and to said mist jet delivery nozzle arrangement; and c) means for applying a suction force to said suction conduit, thereby to cause suctioning from said at least one suction port of liquid and abraded tissue particles in the vicinity of said mist jet delivery nozzle arrangement.

14. The system according to claim 12, wherein gas is supplied from said pressurized gas source at a pressure in the range of 40-150 p.s.i.

15. The system according to claim 12, wherein liquid is supplied from said pressurized liquid source at a pressure in the range of 1 to 5 p.s.i.

16. The system according to claim 12, wherein the gas supplied from said pressurized gas source includes at least one gas selected from: air, oxygen, carbon dioxide and nitrogen.

17. The system according to claim 12, wherein the gas discharged from said at least one gas discharge nozzle is accelerated to a velocity in the range of sub-sonic to supersonic velocity.

18. The system according to claim 12, wherein said mist jet delivery nozzle arrangement includes at least two gas discharge nozzles.

19. The system according to claim 12, wherein said mist jet delivery nozzle arrangement includes at least two liquid discharge nozzles.

20. The system according to claim 12, wherein said at least one gas discharge nozzle is a device configured to have a converging portion, a throat portion and a diverging portion.

21. A device according to claim 20, wherein said at least one gas discharge nozzle is configured such that discharging gas has a cone angle of less than 10 degrees, thereby providing a substantially parallel gas flow.

22. The system according to claim 12, wherein the flow of gas entering said at least one gas discharge nozzle is at a pressure of a first magnitude, and said at least one gas discharge nozzle is operative to cause a pressure drop in the flow of gas therethrough such that the pressure of gas discharged from said at least one gas discharge nozzle is of a second magnitude, wherein the first magnitude is at least twice the second magnitude, so as to cause a shock wave in the flow of gas and the flow of liquid downstream of said at least one gas discharge nozzle and said at least one liquid discharge nozzle so as to cause atomizing of the liquid discharged from said at least one liquid discharge nozzle into a high velocity mist of droplets, thereby to form the mist of accelerated droplets suspended in the flow of discharged high velocity gas.

23. A method of abrading tissue which includes the following steps:

a) accelerating a flow of gas through at least one gas nozzle so as to discharge a gas discharge flow at an elevated velocity into the atmosphere so that the gas discharge flow undergoes a rapid and substantial reduction in pressure to atmospheric pressure;

b) discharging into the atmosphere and introducing into the elevated velocity gas discharge flow a separate flow of liquid, thereby to fragment the liquid into a mist of droplets, and to accelerate the mist to an accelerated velocity similar to the elevated velocity of the gas discharge flow; and c) exposing a desired tissue mass to the accelerated droplet mist.

24. The method according to claim 23, includes an additional step of applying a suction force to a suction conduit, thereby to cause suctioning from at least one suction port of liquid and abraded tissue particles in the vicinity of the gas and mist discharge flow.

25. The method according to claim 23, wherein said step of accelerating a flow of gas includes accelerating the flow of gas to a velocity in the range of sub-sonic to supersonic velocity.

26. The method according to claim 23, wherein said step of accelerating a flow of gas includes accelerating the flow of gas to a velocity in the range of sonic to supersonic velocity.

27. The method according to claim 23, wherein said step of accelerating a flow of gas includes accelerating a gas selected from a group of gases including at least one of air, oxygen, nitrogen and carbon dioxide.

28. The method according to claim 23, wherein said step of introducing into the elevated velocity gas discharge flow the separate flow of liquid, includes the flow of gas entering the at least one gas nozzle being at a pressure of a first magnitude, and the at least one gas nozzle being operative to cause a pressure drop in the gas flow therethrough such that the pressure of the gas discharged from the at least one gas nozzle is of a second magnitude, wherein the first magnitude is at least twice the second magnitude, thereby causing a shock wave in the flow of gas and the flow of liquid downstream of the at least one gas nozzle and at least one liquid discharge nozzle so as to cause atomizing of the liquid discharged from said at least one liquid discharge nozzle into the accelerated velocity mist of droplets, thereby forming a mist of droplets suspended in the flow of discharged elevated velocity gas.

29. The method according to claim 23, wherein said step of exposing a desired tissue mass includes cleansing the tissue mass thereby to remove contaminants from the tissue mass.

30. The method according to claim 23, wherein said step of exposing a desired tissue mass includes dispersing accumulated liquid from the tissue mass by the flow of high velocity gas.

31. The method according to claim 23, wherein said step of exposing a desired tissue mass includes cleansing away and destroying residual anaerobic organisms using a sterile liquid mist in a flow of oxygen gas.

* * * * *